US011305017B2

(12) United States Patent
Poznansky et al.

(10) Patent No.: US 11,305,017 B2
(45) Date of Patent: Apr. 19, 2022

(54) ANTI-FUGETACTIC AGENT AND ANTI-CANCER AGENT COMBINATION THERAPY AND COMPOSITIONS FOR THE TREATMENT OF CANCER

(71) Applicant: The General Hospital Corporation, Boston, MA (US)

(72) Inventors: Mark C. Poznansky, Newton Center, MA (US); Patrick Reeves, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/532,203

(22) Filed: Aug. 5, 2019

(65) Prior Publication Data

US 2020/0093928 A1    Mar. 26, 2020

Related U.S. Application Data

(63) Continuation of application No. 15/568,965, filed as application No. PCT/US2016/029257 on Apr. 25, 2016, now abandoned.

(60) Provisional application No. 62/152,831, filed on Apr. 25, 2015.

(51) Int. Cl.
| | |
|---|---|
| *A61K 45/06* | (2006.01) |
| *A61K 31/396* | (2006.01) |
| *A61K 39/395* | (2006.01) |
| *A61P 35/02* | (2006.01) |
| *C07K 14/52* | (2006.01) |
| *C07K 14/54* | (2006.01) |
| *C07K 16/30* | (2006.01) |

(52) U.S. Cl.
CPC ............ *A61K 45/06* (2013.01); *A61K 31/396* (2013.01); *A61K 39/395* (2013.01); *A61P 35/02* (2018.01); *C07K 14/521* (2013.01); *C07K 14/5421* (2013.01); *C07K 16/30* (2013.01)

(58) Field of Classification Search
CPC ....... A61K 45/06; A61P 35/02; C07K 14/521; C07K 16/30
See application file for complete search history.

(56) References Cited

U.S. PATENT DOCUMENTS

| | | |
|---|---|---|
| 5,075,109 A | 12/1991 | Tice et al. |
| 5,272,082 A | 12/1993 | Santoli et al. |
| 5,514,555 A | 5/1996 | Springer et al. |
| 5,583,131 A | 12/1996 | Bridger et al. |
| 5,858,358 A | 1/1999 | June et al. |
| 5,883,223 A | 3/1999 | Gray |
| 6,352,694 B1 | 3/2002 | June et al. |
| 6,448,054 B1 | 9/2002 | Poznansky et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,618,817 B2 | 11/2009 | Campbell |
| 8,034,332 B2 | 10/2011 | Klingemann |
| 8,034,334 B2 | 10/2011 | Dudley et al. |
| 8,313,943 B2 | 11/2012 | Campbell |
| 8,383,099 B2 | 2/2013 | Dudley et al. |
| 8,906,682 B2 | 12/2014 | June et al. |
| 2002/0068044 A1 | 6/2002 | Klingemann |
| 2006/0121005 A1 | 6/2006 | Berenson et al. |
| 2007/0043012 A1 | 2/2007 | Bridger |
| 2008/0247990 A1 | 10/2008 | Campbell |
| 2008/0300165 A1 | 12/2008 | Poznansky et al. |
| 2011/0281814 A1* | 11/2011 | Dash ................... A61K 31/395 514/34 |
| 2012/0321666 A1 | 12/2012 | Cooper et al. |
| 2014/0065096 A1 | 3/2014 | Ichim et al. |

FOREIGN PATENT DOCUMENTS

| | | |
|---|---|---|
| JP | 2009-504788 A | 2/2009 |
| JP | 2012-516354 A | 7/2012 |
| TW | 201043229 | 12/2010 |
| WO | WO 2006/137934 | 12/2006 |
| WO | WO 2010/040029 | 4/2010 |
| WO | WO 2012/047339 | 4/2012 |
| WO | WO 2013/154760 | 10/2013 |
| WO | WO 2014/055668 | 4/2014 |
| WO | WO 2015/019284 | * 2/2015 |

OTHER PUBLICATIONS

Dubrovska et al. in PLoS One 7(2), e31226, pp. 1-13 (2012) (Year: 2012).*
Figg et al. in Seminars in Oncology, vol. 28, No. 4, Suppl 15 Aug. 2001: pp. 62-66 (Year: 2001).*
Taguchi, T. in Gan To Kagaku Ryoho. Sep. 1984;11(9):1717-28 (English Abstract) (Year: 1984).*
Doughty et al. in Regional Chemotherapy for Breast Cancer pp. 47-49 (1994) (Year: 1994).*
Hiraga et al. in Oncology Reports 25:289-296 (2011) (Year: 2011).*
Suster et al. in World J Stem Cells Jul. 26, 2019; 11(7): 383-397 (Year: 2019).*
Reeves et al., Anti-Cancer Drugs. 2017. 28(91:935-942 (Year: 2017).*

(Continued)

*Primary Examiner* — Dennis Heyer
(74) *Attorney, Agent, or Firm* — Fish & Richardson P.C.

(57) ABSTRACT

The invention described herein relates to methods and compositions for treating cancer in a patient or a tumor cell by administering an effective amount of an anti-fugetactic agent and an additional anti-cancer agent.

16 Claims, No Drawings

(56) References Cited

OTHER PUBLICATIONS

Reeves et al. Anti-Cancer Drugs 28:935-942 (2017) (Year: 2017).*
CN Office Action in Chinese Appln. No. 201680035669.1 dated Feb. 3, 2020, 25 pages (with English translation).
JP Office Action in Japanese Appln. No. 2017-555694, dated Mar. 30, 2020, 10 pages (with English translation).
Dubrovska et al., "CXCR4 Expression in Prostate Cancer Progenitor cells," PLOS ONE, Feb. 2012, 7(2): 7-8.
MX Office Action hi Mexican Appln. No. MX/A/2017/013668, dated Jul. 15, 2020, 6 pages (with Enelish translation).
Bernardini et al., "CCL3 and CXCL12 regulate trafficking of mouse bone marrow NK cell subsets," Blood, The Journal of the American Society of Hematology, Apr. 2008, 111(7):3626-3634.
Domanska et al. °CXCR4 Inhibition with AMD3100 Sensitizes Prostate Cancer to docetaxel chemotherapy, Neoplasia, Aug. 2012, 14(8):709.
Figg et al. "A randomized phase II trial of docetaxel (taxotere) plus thalidomide in androgen-independent prostate cancer," Seminars in Oncology, Aug. 2001, 28(15):62-66.
Fuji et al., "Combination therapy with pacliltaxel and thalidomideinhibits angiogenesis and growth of human colon cancer xenograft in mice," Anticancer Res., 2003, 23(3B):2405-2411.
Glienke et al., "Advantages and applications of CAR-expressing natural killer cells," Frontiers in Pharmacology (Feb. 2015).
Notification Concerning Transmittal of International Preliminary Report on Patentability corresponding to International Application No. PCT/US2016/029254 dated Nov. 9, 2017.
PCT International Search Report and Written Opinion in International Appln. No. PCT/US2016/029254, dated Jul. 18, 2016.
PCT International Search Report and Written Opinion in International Appln. No. PCT/US2016/029257, dated Jun. 29, 2016.
Righi et al., "CXCL12/CXCR4 Blockade Induces Multimodal Antitumor Effects that Prolong Survival in an immunocompetent Mouse Model of Ovarian Cancer," Cancer Research, Aug. 2011, 15(71):5522-5534.
Santini et al., "A controlled-release microchip," Nature, Jan. 1999, 397(6717):335-338.
Scott et al., "Monoclonal antibodies in cancer therapy," Cancer Immunity, 2012, 12:14, 8 pages.
Transmittal of international Preliminary Report on Patentability corresponding to International Application No. PCT/US2016/029257 dated Nov. 9, 2017.
Voloshin et al., "G-CSF supplementation with chemotherapy can promote revascularization and subsequent tumor regrowth: prevention by a CXCR4 antagonist," The Journal of the American Society of Hematology, Sep. 2011, 118(12):3426-3435.
Fujii et al., "Combination therapy with paclitaxel and thalidomide inhibits angiogenesis and growth of human colon cancer xenograft in mice," Anticancer Res., 2003, 23(3B):2405-2411, Abstract Only.
IN Office Action in Indian Appln. No. 201747041370, dated Sep. 11, 2020, 6 pages.
Reeves et al., "CXCR4 blockade with AMD3100 enhances Taxol chemotherapy to limit ovarian cancer cell growth," Anti-Cancer Drugs, 2017, 28(9):935-942.

* cited by examiner

ANTI-FUGETACTIC AGENT AND ANTI-CANCER AGENT COMBINATION THERAPY AND COMPOSITIONS FOR THE TREATMENT OF CANCER

RELATED APPLICATIONS

This application is a continuation of and claims priority to U.S. patent application Ser. No. 15/568,965, filed Oct. 24, 2017 which is a 35 U.S.C. § 371 national phase application of PCT Application PCT/US2016/029257 filed Apr. 25, 2016, which claims the benefit, under 35 U.S.C. § 119(e), of U.S. Provisional Application No. 62/152,831, filed Apr. 25, 2015, the entire contents of each of which are incorporated by reference herein.

BACKGROUND OF THE INVENTION

Cell movement in response to specific stimuli is observed to occur in prokaryotes and eukaryotes. Cell movement seen in these organisms has been classified into three types: chemotaxis or the movement of cells along a gradient towards an increasing concentration of a chemical; negative chemotaxis which has been defined as the movement down a gradient of a chemical stimulus; and chemokinesis or the increased random movement of cells induced by a chemical agent.

Chemotaxis and chemokinesis have been observed to occur in mammalian cells in response to the class of proteins, called chemokines. Additionally, chemorepellent, or fugetactic, activity has been observed in mammalian cells. For example, some tumor cells secrete concentrations of chemokines that are sufficient to repel immune cells from the site of a tumor, thereby reducing the immune system's ability to target and eradicate the tumor. Metastasizing cancer cells may use a similar mechanism to evade the immune system.

Anti-fugetactic agents have been described that inhibit the fugetactic activity of tumor cells and allow the patient's immune system to target the tumor (see US 2008/0300165, incorporated herein by reference in its entirety). However, treatment with such agents may not be sufficient to eradicate a tumor in all patients, depending on the type of tumor, size of tumor, number of metastases, site(s) of metastasis, patient's health, etc.

There remains a need for treatments and compositions that target tumors to efficiently kill tumors and/or metastasizing cancer cells.

SUMMARY OF THE INVENTION

This invention relates to the treatment of a tumor with an anti-fugetactic agent in combination with one or more additional anti-cancer therapies. The one or more additional cancer therapies may include chemotherapy, proton beam therapy, radiotherapy, immunotherapy, antibody therapy, cell therapy, and/or vaccine therapy.

Repulsion of tumor antigen-specific T-cells. e.g. from a tumor expressing high levels of CXCL12 or interleukin 8 (IL-8), allows the tumor cells to evade immune control. This invention is predicated on the discovery that treatment with an effective amount of anti-fugetactic agent for a period of time sufficient to provide attenuate the fugetactic effect of the chemokine restores immune defenses against tumors, and also allow anti-cancer agents (e.g., chemotherapeutic agents, radiotherapeutic agents, and the like) to better access the tumor in order to reduce or eradicate the tumor. Without being bound by theory, it is believed that co-administration of the agents as described herein will lead to a synergistic response in a patient with a tumor, such that the patient has a better outcome than with either therapy alone. Anti-cancer agents include, without limitation, traditional cancer therapies, e.g. chemotherapy, radiotherapy, and/or vaccine therapy.

Although anti-fugetactic agents alone provide promising results for cancer treatment, it is believed that combination therapy as described herein will result in more efficient tumor targeting and better patient outcomes. Without being bound by theory, it is believed that such methods are especially beneficial, by way of non-limiting example, if the tumor is large in size, there are multiple tumors in the patient, the patient's immune system is compromised, etc.

As many as 85% of solid tumors and leukemias express CXCL12 at a level sufficient to have fugetactic effects, e.g. repulsion of immune cells from the tumor. Cancers that express CXCL12 at such levels include, but are not limited to, prostate cancer, lung cancer, breast cancer, pancreatic cancer, ovarian cancer, gastric cancer, esophageal cancer, and leukemia.

One embodiment of the invention relates to a composition for cancer therapy, the composition comprising an anti-fugetactic agent and at least one additional anti-cancer agent. In one embodiment, the at least one additional anti-cancer agent is a chemotherapeutic agent, a radiotherapy agent, and/or an anti-cancer vaccine. In other embodiments, the additional anti-cancer agent is selected from immunotherapy, vaccine therapy, ceil therapy, and antibody therapy.

One embodiment of the invention relates to a method for treating cancer in a patient in need thereof, the method comprising administering to the patient an anti-fugetactic agent and at least one additional anti-cancer agent.

One embodiment of the invention relates to a method for increasing migration of immune cells to a tumor site in a patient having a cancer, the method comprising administering to the patient an anti-fugetactic agent and at least one additional anti-cancer agent.

One embodiment of the invention relates to a method for inhibiting tumor cell metastasis in a patient in need thereof, the method comprising administering to the patient an anti-fugetactic agent and at least one additional anti-cancer agent.

One embodiment of the invention relates to a method for locally treating a solid tumor in a mammal, the method comprising administering to the patient an anti-fugetactic agent and at least one additional anti-cancer agent.

One embodiment of the invention relates to a method for treating a cancer cell, the method comprising administering to the patient an anti-fugetactic agent and at least one additional anti-cancer agent.

In a preferred embodiment, the cancer, tumor, or cell expresses an amount of a chemokine sufficient to produce a fugetactic effect. In one embodiment, the chemokine is secreted by the cell or tumor, such that the fugetactic effect is present in the tumor microenvironment. In one embodiment, the concentration of the chemokine in the tumor microenvironment is greater than about 100 nM prior to treatment with the anti-fugetactic agent. In one embodiment, the chemokine is CXCL12 or IL-8. In a preferred embodiment, the chemokine is CXCL12.

In one embodiment, the tumor is a solid tumor. In one embodiment, the tumor is a non-solid tumor. In one embodiment, the tumor is a leukemia.

In one embodiment, the at least one additional anti-cancer agent is a chemotherapeutic agent, a radiotherapy agent, and/or an anti-cancer vaccine.

Without being bound by theory, it is believed that the combination therapy as described herein will allow the targeting of a tumor by the patient's own immune cells, as well as by the additional anti-cancer agent. For example, the patient's immune system can be used to target a tumor or metastatic tumor cells in combination with the additional anti-cancer agent(s).

The anti-fugetactic agent may be any such agent known in the art. In one embodiment, the anti-fugetactic agent is an anti-fugetactic agent as described in U.S. Patent Application Publication No. 2008/0300165, which is hereby incorporated by reference in its entirety. In a preferred embodiment, the anti-fugetactic agent is selected from the group consisting of AMD3100 (mozobil/plerixafor), KRH-1636, T-20, T-22, T-140, TE-14011, T-14012, TN14003, TAK-779, AK602, SCH-351125, Tannic acid, NSC 651016, thalidomide, GF 109230X, and an antibody that interferes with dimerization of a fugetactic chemokine or the receptor for a fugetactic chemokine. For example, the antibody may inhibit dimerization of CXCL12, IL-8, CXCR3, or CXCR4. In one embodiment, the anti-fugetactic agent is an antibody that interferes with binding of the chemokine to its receptor. In an especially preferred embodiment, the anti-fugetactic agent is AMD3100.

The anti-fugetactic agent is administered in combination with at least one anti-cancer therapy/agent. "In combination" refers to any combination, including sequential or simultaneous administration. In one embodiment, the anti-fugetactic agent is administered separately from the anti-cancer therapy/agent. In one embodiment, the anti-fugetactic agent is administered in a single composition with the anti-cancer agent(s).

In one embodiment, the anti-fugetactic agent and/or anti-cancer agent is administered intravenously, subcutaneously, orally, or intraperitoneally. In a preferred embodiment, the anti-fugetactic agent is administered proximal to (e.g., near or within the same body cavity as) the tumor. In one embodiment, the anti-fugetactic agent is administered directly into the tumor or into a blood vessel feeding the tumor. In one embodiment, the anti-fugetactic agent is administered systemically. In a further embodiment, the anti-fugetactic agent is administered by microcatheter, or an implanted device, and an implanted dosage form.

In one embodiment, the anti-fugetactic agent is administered in a continuous manner for a defined period. In another embodiment, anti-fugetactic agent is administered in a pulsatile manner. For example, the anti-fugetactic agent may be administered intermittently over a period of time.

In a preferred embodiment, the anti-fugetactic agent and anti-cancer agent(s) are administered sequentially. For example, the anti-fugetactic agent may be administered for a period of time sufficient to reduce or attenuate the fugetactic effect of the tumor, e.g. such that the anti-fugetactic agent has an anti-fugetactic effect; the anti-cancer agent can then be administered for a period of time during which the fugetactic effect of the tumor is reduced or attenuated. In one embodiment, the anti-fugetactic agent and anti-cancer agent are administered sequentially in an alternating manner at least until the condition of the patient improves. Improvement of the condition of the patient includes, without limitation, reduction in tumor size, a reduction in at least one symptom of the cancer, elimination of the tumor and/or metastases thereof, increased survival of the patient, and the like.

Without being bound by theory, it is believed that the anti-fugetactic agent will reduce the fugetactic effect of the chemokine-secreting tumor or cancer cell so as to allow better access to the tumor or cell by additional agents and immune cells. The anti-cancer agent(s) may be subsequently administered, e.g. during a period of time during which the fugetactic effect of the tumor or cell is reduced. In a preferred embodiment, the sequential administration of the anti-fugetactic agent and anti-cancer agent is repeated at least until the patient's condition improves. In one embodiment, the sequential administration of the agents is repeated until the tumor is eradicated.

In one embodiment, the anti-fugetactic agent and/or the at least one additional anti-cancer agent are administered directly to the tumor site. In one embodiment, the anti-fugetactic agent and/or the at least one additional anti-cancer agent are administered by direct injection into the tumor. In one embodiment, the anti-fugetactic agent and/or the at least one additional anti-cancer agent are administered proximal to the tumor site. In a preferred embodiment, the anti-fugetactic agent and/or the at least one additional anti-cancer agent are administered directly into a blood vessel associated with the tumor (e.g., via microcatheter injection into the blood vessels in, near, or feeding into the tumor).

This invention further relates to a kit of parts for treating cancer in a patient, the kit of parts comprising an anti-fugetactic agent and at least one additional anti-cancer agent as described herein. Optionally, the kit comprises instructions for dosing of the anti-fugetactic agent and/or the at least one additional anti-cancer agent. In one embodiment, this invention relates to the use of an anti-fugetactic agent and at least one additional anti-cancer agent to treat a patient with cancer.

This invention further relates to a tumor cell from a chemokine-expressing tumor, said cell having been contacted with an anti-fugetactic agent and at least one additional anti-cancer agent. In one embodiment, the chemokine is CXCL12. In one embodiment, the chemokine is IL-8.

DETAILED DESCRIPTION

After reading this description, it will become apparent to one skilled in the art how to implement the invention in various alternative embodiments and alternative applications. However, not all embodiments of the present invention are described herein. It will be understood that the embodiments presented hero are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Definitions

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" or "comprises" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g. horse, cow, pig, goat, sheep). In especially preferred embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. For example, treatment of a cancer or tumor includes, but is not limited to, reduction in size of the tumor, elimination of the tumor and/or metastases thereof, remission of the cancer, inhibition of metastasis of the tumor, reduction or elimination of at least one symptom of the cancer, and the like.

The term "administering" or "administration" of an agent, drug, or a natural killer cell to a subject includes any route of introducing or delivering to a subject a compound to perform its intended function. Administration can be carried out by any suitable route, including orally, intranasally, parenterally (intravenously, intramuscularly, intraperiloneally, or subcutaneously), or topically. Administration includes self-administration and the administration by another.

It is also to be appreciated that the various modes of treatment or prevention of medical diseases and conditions as described are intended to mean "substantial," which includes total but also less than total treatment or prevention, and wherein some biologically or medically relevant result is achieved.

The term "separate" administration refers to an administration of at least two active ingredients at the same time or substantially the same time by different routes.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

The term "simultaneous" therapeutic use refers to the administration of at least two active ingredients by the same route and at the same time or at substantially the same time.

The term "therapeutic" as used herein means a treatment and/or prophylaxis. A therapeutic effect is obtained by suppression, remission, or eradication of a disease state.

The term "therapeutically effective amount" or "effective amount" refers to an amount of the agent that, when administered, is sufficient to cause tire desired effect. For example, an effective amount of an anti-fugetactic agent may be an amount sufficient to have an anti-fugetactic effect on a cancer cell or tumor (e.g. to attenuate a fugetactic effect from the tumor or cancer cell). The therapeutically effective amount of the agent will vary depending on the tumor being treated and its severity as well as the age, weight, etc., of the patient to be treated. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

The term "kill" with respect to a cell/cell population is directed to include any type of manipulation that will lead to the death of that cell/cell population.

"Antibodies" as used herein include polyclonal, monoclonal, single chain, chimeric, humanized and human antibodies, prepared according to conventional methodology.

"Cytokine" is a generic term for non-antibody, soluble proteins which are released from one cell subpopulation and which act as intercellular mediators, for example, in the generation or regulation of an immune response. See Human Cytokines: Handbook for Basic & Clinical Research (Aggrawal, et al. eds., Blackwell Scientific, Boston, Mass. 1991) (which is hereby incorporated by reference in its entirety for all purposes).

"CXCR4/CXCL12 antagonist" refers to a compound that antagonizes CXCL12 binding to CXCR4 or otherwise reduces the fugetactic effect of CXCL12.

By "fugetactic activity" it is meant the ability of an agent to repel (or chemorepel) a eukaryotic cell with migratory capacity (i.e., a cell that can move away from a repellant stimulus). Accordingly, an agent with fugetactic activity is a "fugetactic agent." Such activity can be detected using any of a variety of systems well known in the art (see, e.g., U.S. Pat. No. 5,514,555 and U.S. Patent Application Pub. No. 2008/0300165, each of which is incorporated by reference herein in its entirety). A preferred system for use herein is described in U.S. Pat. No. 6,448,054, which is incorporated herein by reference in its entirety.

The term "fugetactic effect" refers to the chemorepellant effect of a chemokine secreted by a cell, e.g. a tumor cell. Usually, the fugetactic effect is present in an area around the cell wherein the concentration of the chemokine is sufficient to provide the fugetactic effect. Some chemokines, including interleukin 8 and CXCL12, may exert fugetactic activity at high concentrations (e.g., over about 100 nM), whereas lower concentrations exhibit no fugetactic effect and may even be chemoattractant.

The term "anti-fugetactic effect" refers to the effect of the anti-fugetactic agent to attenuate or eliminate the fugetactic effect of the chemokine.

"Immune cells" as used herein are cells of hematopoietic origin that are involved in the specific recognition of antigens. Immune cells include antigen presenting cells (APCs), such as dendritic cells or macrophages, B cells, T cells, etc.

The term "anti-cancer therapy" as used herein refers to traditional cancer treatments, including chemotherapy and radiotherapy, as well as vaccine therapy.

Anti-Fugetactic Agents

Many tumors have fugetactic effects, e.g. on immune cells, due to chemokines secreted by the tumor cells. High concentrations of the chemokines secreted by the tumor cells can have fugetactic (chemorepellant) effects on cells, whereas lower concentrations do not have such effects or even result in chemoattraction. For example, T-cells are repelled by CXCL12 (SDF-1) by a concentration-dependent and CXCR4 receptor-mediated mechanism. This invention is predicated on the surprising discovery that anti-fugetactic agents as described herein reduce the fugetactic effects of the tumors, thereby allowing immune cells and other anti-cancer agents to better access and kill the tumor cells.

The anti-fugetactic agent may be any such agent known in the art, for example an anti-fugetactic agent as described in U.S. Patent Application Publication No. 2008/0300165, which is hereby incorporated by reference in its entirety.

Anti-fugetactic agents include any agents that specifically inhibit chemokine and/or chemokine receptor dimerization, thereby blocking the chemorepellent response to a fugetactic agent. Certain chemokines, including IL-8 and CXCL12 can also serve as chemorepellents at high concentrations (e.g., above 100 nM) where much of the chemokine exists as a dimer. Dimerization of the chemokine elicits a differential response in cells, causing dimerization of chemokine receptors, an activity which is interpreted as a chemorepellent signal. Blocking the chemorepellent effect of high concentrations of a chemokine secreted by a tumor can be accomplished, for example, by anti-fugetactic agents which inhibit chemokine dimer formation or chemokine receptor dimer formation. For example, antibodies that target and block chemokine receptor dimerization, for example, by interfering with the dimerization domains or ligand binding can be anti-fugetactic agents. Anti-fugetactic agents that act via other mechanisms of action, e.g. that reduce the amount of fugetactic cytokine secreted by the cells, inhibit dimerization, and/or inhibit binding of the chemokine to a target receptor, are also encompassed by the present invention. Where desired, this effect can be achieved without inhibiting the chemotactic action of monomeric chemokine.

In other embodiments, the anti-fugetactic agent is a CXCR4 antagonist, CXCR3 antagonist, CXCR4/CXCL12 antagonist or selective PKC inhibitor.

The CXCR4 antagonist can be but is not limited to AMD3100, KRH-1636, T-20, T-22, T-140, TE-14011, T-14012, or TN14003, or an antibody that interferes with the dimerization of CXCR4.

The CXCR3 antagonist can be but is not limited to TAK-779, AK602, or SCH-351125, or an antibody that interferes with the dimerization of CXCR3.

The CXCR4/CXCL12 antagonist can be but is not limited to Tannic acid, NSC 651016, or an antibody that interferes with the dimerization of CXCR4 and/or CXCL12.

The selective PKC inhibitor can be but is not limited to thalidomide or GF 109230X.

In a preferred embodiment, the anti-fugetactic agent is AMD3100 (plerixafor). AMD3100 is described in U.S. Pat. No. 5,583,131, which is incorporated by reference herein in its entirety.

In one embodiment, the anti-fugetactic agent is coupled with a molecule that allows targeting of a tumor. In one embodiment, the anti-fugetactic agent is coupled with (e.g., bound to) an antibody specific for the tumor to be targeted. In one embodiment, the anti-fugetactic agent coupled to the molecule that allows targeting of the tumor is administered systemically.

CXCL12 expression by a tumor may also promote tumor growth, angiogenesis, and metastasis. Accordingly, methods for inhibiting tumor growth, angiogenesis, and metastasis are contemplated by this invention.

In one embodiment, the anti-fugetactic agent is administered in combination with an additional compound that enhances the anti-fugetactic activity of the agent. In one embodiment, the additional compound is granulocyte colony stimulating factor (G-CSF). In one embodiment, G-CSF is not administered.

Chemotherapy Agents

In one aspect of the present invention, an anti-fugetactic agent is administered in combination with a chemotherapy agent. The chemotherapy agent may be any agent having a therapeutic effect on one or more types of cancer. Many chemotherapy agents are currently known in the art. Types of chemotherapy drugs include, by way of non-limiting example, alkylating agents, antimetabolites, anti-tumor antibiotics, totpoisomerasc inhibitors, mitotic inhibitors, corticosteroids, and the like.

Non-limiting examples of chemotherapy drugs include: nitrogen mustards, such as mechlorethamine (nitrogen mustard), chlorambucil, cyclophosphamide (Cytoxan®), ifosfamide, and melphalan); Nitrosoureas, such as streptozocin, carmustine (BCNU), and lomustine; alkyl sulfonates, such as busulfan; Triazines, such as dacarbazine (DITC) and temozolomide (Temodar®); ethylenimines, such as thiotepa and altretamine (hexamethylmelamine); platinum drugs, such as cisplatin, carboplatin, and oxalaplatin; 5-fluorouracil (5-FU); 6-mercaptopurine (6-MP); Capecitabine (Xeloda®); Cytarabine (Ara-C®); Floxuridine; Fludarabine; Gemcitabine (Gemzar®); Hydroxyurea; Methotrexate; Pemelrexed (Alimta®); anthracyclines, such as Daunorubicin, Doxorubicin (Adriamycin®), Epirubicin, Idarubicin; Actinomycin-D; Bleomycin; Mitomycin-C; Mitoxantrone; Topotecan; Irinotecan (CPT-11); Etoposide (VP-16); Teniposide; Mitoxantrone; Taxanes: paelitaxel (Taxol®) and docetaxel (Taxotere®); Epothilones; ixabepilone (Ixempra®); Vinca alkaloids: vinblastine (Velban®), vincristine (Oncovin®), and vinorelbine (Navelbine®); Estramustine (Emcyt®); Prednisone; Methylprednisolone (Solumedrol®); Dexamethasone (Decadron®); L-asparaginase; bortezomib (Velcade®). Additional chemotherapy agents are listed, for example, in U.S. Patent Application Pub. No. 2008/0300165, which is incorporated herein by reference in its entirety.

Doses and administration protocols for chemotherapy drugs are well-known in the art. The skilled clinician can readily determine the proper dosing regimen to be used, based on factors including the chemotherapy agent(s) administered, type of cancer being treated, stage of the cancer, age and condition of the patient, patient size, location of the tumor, and the like.

Radiotherapy Agents

In one aspect of the present invention, an anti-fugetactic agent is administered in combination with a radiotherapeutic agent. The radiotherapeutic agent may be any such agent having a therapeutic effect on one or more types of cancer. Many radiotherapeutic agents are currently known in the art. Types of radiotherapeutic drugs include, by way of non-limiting example, X-rays, gamma rays, and charged particles. In one embodiment, the radiotherapeutic agent is delivered by a machine outside of the body (external-beam radiation therapy). In a preferred embodiment, the radiotherapeutic agent is placed in the body near the tumor/cancer cells (brachytherapy) or is a systemic radiation therapy.

External-beam radiation therapy may be administered by any means. Exemplary, non-limiting types of external-beam radiation therapy include linear accelerator-administered radiation therapy, 3-dimensional conformal radiation therapy (3D-CRT), intensity-modulated radiation therapy (IMRT), image-guided radiation therapy (IGRT), tomotherapy, stereotactic radiosurgery, photon therapy, stereotactic body radiation therapy, proton beam therapy, and electron beam therapy.

Internal radiation therapy (brachytherapy) may be by any technique or agent. Exemplary, non-limiting types of internal radiation therapy include any radioactive agents that can be placed proximal to or within the tumor, such as Radium-226 (Ra-226), Cobalt-60 (Co-60), Cesium-137 (Cs-137), cesium-131, Iridium-192 (Ir-192), Gold-198 (Au-198), Iodine-125 (I-125), palladium-103, yttrium-90, etc. Such agents may be administered by seeds, needles, or any other route of administration, and may be temporary or permanent.

Systemic radiation therapy may be by any technique or agent. Exemplary, non-limiting types of systemic radiation therapy include radioactive iodine, ibritumomab tiuxetan (Zevalin®), tositumomab and iodine 1131 tositumomab (Bexxar®), samarium-153-lexidronam (Quadramet®), strontium-89 chloride (Metastron®), metaiodobenzylguanidine, lutetium-177, yttrium-90, strontium-89, and the like.

In one embodiment, a radiosensitizing agent is also administered to the patient. Radiosensitizing agents increase the damaging effect of radiation on cancer cells.

Doses and administration protocols for radiotherapy agents are well-known in the art. The skilled clinician can readily determine the proper dosing regimen to be used, based on factors including the agent(s) administered, type of cancer being treated, stage of the cancer, location of the tumor, age and condition of the patient, patient size, and the like.

Anti-Cancer Vaccines

In one aspect of the present invention, an anti-fugetactic agent is administered in combination with an anti-cancer vaccine (also called cancer vaccine). Anti-cancer vaccines are vaccines that either treat existing cancer or prevent development of a cancer by stimulating an immune reaction to kill the cancer cells. In a preferred embodiment, the anti-cancer vaccine treats existing cancer.

The anti-cancer vaccine may be any such vaccine having a therapeutic effect on one or more types of cancer. Many anti-cancer vaccines are currently known in the art. Such vaccines include, without limitation, dasiprotimut-T, Sipuleucel-T, talimogene laherparepvec, HSPPC-96 complex (Vitespen), L-BLP25, gp100 melanoma vaccine, and any other vaccine that stimulates an immune response to cancer cells when administered to a patient.

Cancers

Cancers or tumors that can be treated by the compounds and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In a preferred embodiment, the tumor is a solid tumor. In one embodiment, the tumor is a leukemia. In an especially preferred embodiment, the tumor over-expresses CXCL12. In one embodiment, tumor expression of CXCL12 can be evaluated prior to administration of a composition as described herein. For example, a patient having a tumor that is determined to express or over-express CXCL12 will be treated using a method and/or composition as described herein.

In one embodiment, the tumor is a brain tumor. It is contemplated that a brain tumor, e.g., an inoperable brain tumor, can be injected with a composition described herein. In one embodiment, an anti-fugetactic agent is administered directly to a brain tumor via a catheter into a blood vessel within or proximal to the brain tumor. Further discussion of catheter or microcatheter administration is described below.

Dose and Administration

The compositions, as described herein, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result.

The anti-cancer agent may be administered by any appropriate method. Dosage, treatment protocol, and routes of administration for anti-cancer agents, including chemotherapeutic agents, radiotherapeutic agents, and anti-cancer vaccines, are known in the art and/or within the ability of a skilled clinician to determine, based on the type of treatment, type of cancer, etc.

Generally, the dose of the anti-fugetactic agent of the present invention is from about 5 mg/kg body weight per day to about 50 mg/kg per day, inclusive of all values and ranges therebetween, including endpoints. In one embodiment, the dose is from about 10 mg/kg to about 50 mg/kg per day. In one embodiment, the dose is from about 10 mg/kg to about 40 mg/kg per day. In one embodiment, the dose is from about 10 mg/kg to about 30 mg/kg per day. In a preferred embodiment, the dose is from about 10 mg/kg to about 20 mg/kg per day. In one embodiment, the dose does not exceed about 50 mg per day.

In one embodiment, the dose of the anti-fugetactic agent is from about 50 mg/kg per week to about 350 mg/kg per week, inclusive of all values and ranges therebetween, including endpoints. In one embodiment, the dose of the anti-fugetactic agent is about 50 mg/kg per week. In one embodiment, the dose of the anti-fugetactic agent is about 60 mg/kg per week. In one embodiment, the dose of the anti-fugetactic agent is about 70 mg/kg per week. In one embodiment, the dose of the anti-fugetactic agent is about 80 mg/kg per week. In one embodiment the dose of the anti-fugetactic agent is about 90 mg/kg per week. In one embodiment, the dose of the anti-fugetactic agent is about 100 mg/kg per week. In one embodiment, the dose of the anti-fugetactic agent is about 110 mg/kg per week. In one embodiment, the dose of the anti-fugetactic agent is about 120 mg/kg per week. In one embodiment, the dose of the anti-fugetactic agent is about 130 mg/kg per week. In one embodiment, the dose of the anti-fugetactic agent is about 140 mg/kg per week. In one embodiment, the dose of the anti-fugetactic agent is about 150 mg/kg per week. In one embodiment, the dose of the anti-fugetactic agent is about 160 mg/kg per week. In one embodiment, the dose of the anti-fugetactic agent is about 170 mg/kg per week. In one embodiment, the dose of the anti-fugetactic agent is about 180 mg/kg per week. In one embodiment, the dose of the anti-fugetactic agent is about 190 mg/kg per week. In one embodiment, the dose of the anti-fugetactic agent is about 200 mg/kg per week. In one embodiment, the dose of the anti-fugetactic agent is about 210 mg/kg per week. In one embodiment, the dose of the anti-fugetactic agent is about 220 mg/kg per week. In one embodiment, the dose of the anti-fugetactic agent is about 230 mg/kg per week. In one embodiment, the dose of the anti-fugetactic agent is about 240 mg/kg per week. In one embodiment, the dose of the anti-fugetactic agent is about 250 mg/kg per week. In one embodiment, the dose of the anti-fugetactic agent is about 260 mg/kg per week. In one embodiment, the dose of the anti-fugetactic agent is about 270 mg/kg per week. In one embodiment, the dose of the anti-fugetactic agent is about 280 mg/kg per week. In one embodiment, the dose of the anti-fugetactic agent is about 290 mg/kg per week. In one embodiment, the dose of the anti-fugetactic agent is about 300 mg/kg per week. In one embodiment, the dose of the anti-fugetactic agent is about 310 mg/kg per week. In one embodiment, the dose of the anti-fugetactic agent is about 320 mg/kg per week. In one embodiment, the dose of the anti-fugetactic agent is about 330 mg/kg per week. In one embodiment, the dose of the anti-fugetactic agent is about 340 mg/kg per week. In one embodiment, the dose of the anti-fugetactic agent is about 350 mg/kg per week.

In one aspect of the invention, the anti-fugetactic agent and the anti-cancer agent(s) are administered sequentially. That is, the anti-fugetactic agent is administered for a period of time sufficient to have an anti-fugetactic effect, and the anti-cancer agent is subsequently administered.

In one aspect of the invention, administration of the anti-fugetactic agent is pulsatile. In one embodiment, an amount of anti-fugetactic agent is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of anti-fugetactic agent is administered every 1 day, 2 days, 3 days, 4 days, 5 days, 6 days, 7 days, 8 days, 9 days, or 10 days.

In one aspect of the invention, doses of the anti-fugetactic agent are administered in a pulsatile manner for a period of time sufficient to have an anti-fugetactic effect (e.g. to attenuate the fugetactic effect of the tumor cell). In one embodiment, the period of time is between about 1 day and about 10 days. For example, the period of time may be 1 day, 2 days, 3 days, 4 days, 5 days, 6 days, 7 days, 8 days, 9 days, or 10 days.

In one aspect of the invention, the anti-cancer agent is administered after the period of time of administration of anti-fugetactic agent. In one embodiment, the anti-cancer agent is administered during a period of time wherein the fugetactic effect of the cancer cells/tumor is attenuated by the anti-fugetactic agent. The length of time and modes of administration of the anti-cancer agent will vary, depending on the anti-cancer agent used, type of tumor being treated, condition of the patient, and the like. Determination of such parameters is within the capability of the skilled clinician.

In one embodiment, administration of the anti-fugetactic agent and the anti-cancer agent is alternated. In a preferred embodiment, administration of the anti-fugetactic agent and the anti-cancer agent is alternated until the condition of the patient improves. Improvement includes, without limitation, reduction in size of the tumor and/or metastases thereof, elimination of the tumor and/or metastases thereof, remission of the cancer, and/or attenuation of at least one symptom of the cancer.

A variety of administration routes are available. The methods of the invention, generally speaking may be practiced using any mode of administration that is medically acceptable, meaning any mode that produces effective levels of the active compounds without causing clinically unacceptable adverse effects.

Modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent(s). Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed 25 oils. Intravenous vehicles include fluid and nutrient replenishes, electrolyte replenishes (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In one embodiment, the anti-fugetactic agent is administered parenterally. In one embodiment, the anti-fugetactic agent is administered via microcatheter into a blood vessel proximal to a tumor. In one embodiment, the anti-fugetactic agent is administered via microcatheter into a blood vessel within a tumor. In one embodiment, the anti-fugetactic agent is administered subcutaneously. In one embodiment, the anti-fugetactic agent is administered intradermally.

Other delivery systems can include time-release, delayed release or sustained release delivery systems. Such systems can avoid repeated administrations of the anti-fugetactic agent, increasing convenience to the subject and the physician. Many types of release delivery systems are available and known to those of ordinary skill in the art. They include polymer base systems such as poly(lactide-glycolide), copolyoxalates, polycaprolaciones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like.

In one embodiment, the anti-fugetactic agent is administered in a time-release delayed release or sustained release delivery system. In one embodiment, the time-release, delayed release or sustained release delivery system comprising the anti-fugetactic agent is inserted directly into the tumor. In one embodiment, the time-release, delayed release or sustained release delivery system comprising the anti-fugetactic agent is implanted in the patient proximal to the tumor. Additional implantable formulations are described, for example, in U.S. Patent App. Pub. No. 2008/0300165, which is incorporated herein by reference in its entirety.

In addition, important embodiments of the invention include pump-based hardware delivery systems, some of which are adapted for implantation. Such implantable pumps include controlled-release microchips. A preferred controlled-release microchip is described in Santini, J T Jr. et al., Nature, 1999, 397:335-338, the contents of which are expressly incorporated herein by reference.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Methods of Treatment

In one aspect of this invention is provided a method for treating cancer in a patient in need thereof by administration of an anti-fugetactic agent. In a preferred embodiment, the anti-fugetactic agent is administered in combination with at least one additional anti-cancer agent.

In one aspect, this invention relates to inhibition of metastasis of a tumor in a patient in need thereof by administration of an anti-fugetactic agent. Without being bound be theory, it is believed that the anti-fugetactic agents as described herein can mobilize cancer cells out of niches where they are otherwise inaccessible to treatments and/or immune cells, and into the circulation where the cells can be targeted by anti-cancer agents and/or immune cells. Surprisingly, such mobilization does not lead to increased metastasis of the tumor, but rather decreases metastasis.

In one aspect, this invention relates to a method for killing a cancer cell expressing an amount of a chemokine sufficient to produce a fugetactic effect, which method comprises:

a) periodically contacting said cell with an effective amount of an anti-fugetactic agent for a sufficient period of time so as to attenuate said fugetactic effect;

b) contacting said cell with at least one anti-cancer agent; and c) optionally repeating a) and b) as necessary to kill said cell.

In one aspect, this invention relates to a method for treating a tumor in a mammal, said tumor expressing an amount of a chemokine sufficient to produce a fugetactic effect, which method comprises:

a) periodically administering to said mammal an effective amount of an anti-fugetactic agent for a sufficient period of time so as to attenuate said fugetactic effect;

b) administering to said mammal at least one anti-cancer agent; and c) optionally repeating a) and b) as necessary to provide an improvement in the condition of the mammal.

In one embodiment, the anti-cancer agent is administered after the period of time of administration of the anti-fugetactic agent. In one embodiment, the anti-cancer agent is administered during a period of time when the fugetactic effect is attenuated.

In one embodiment, the chemokine is CXCL12. In one embodiment, the cancer cell is a solid tumor cell. In one embodiment, the cancer cell is a leukemia cell. In one embodiment, the anti-cancer agent is administered within about 3 days of completion of contacting the cell with the anti-fugetactic agent. In one embodiment, the anti-cancer agent is administered within about 1 day of completion of contacting the cell with the anti-fugetactic agent.

In one aspect, this invention relates to a method for treating a solid tumor in a mammal which tumor expresses CXCL12 at a concentration sufficient to produce a fugetactic effect, the method comprising administering to said mammal an effective amount of an anti-fugetactic agent for a sufficient period of time so as to inhibit said fugetactic effect, followed by administering to said mammal at least one anti-cancer agent. In one embodiment, the cancer cell is a solid tumor cell. In one embodiment, the cancer cell is a leukemia cell. In one embodiment, the anti-cancer agent is administered within about 3 days of completion of administration of the anti-fugetactic agent. In one embodiment, the anti-cancer agent is administered within about 1 day of completion of administration of the anti-fugetactic agent.

In one aspect, this invention relates to solid tumor cell expressing a chemokine, which cell has been contacted with an anti-fugetactic agent and a chemotherapeutic agent. In one embodiment, the chemokine is CXCL12. In one embodiment, the cancer cell is a solid tumor cell. In one embodiment, the cancer cell is a leukemia cell.

In one aspect, this invention relates to a method to locally treat a solid tumor expressing CXCL12 at a concentration sufficient to produce a fugetactic effect in a patient, which method comprises:

a) identifying an artery or microartery feeding said tumor;
b) intra-arterially placing a catheter or microcatheter in said artery or microartery proximal to the flow of blood into said tumor wherein said catheter or microcatheter comprising a lumen for delivering a fluid there through and means for delivering said fluid;
c) periodically administering an effective amount of the anti-fugetactic agent through said catheter or said microcatheter to the artery or microartery feeding said tumor so as to inhibit said fugetactic effect fugetaxis induced by said tumor; and
d) subsequently administering an effective amount of the anti-cancer agent to the patient.

In one embodiment, the tumor is a brain tumor.

In one embodiment, the anti-cancer agent is administered using a catheter, a microcatheter, an external radiation source, or is injected or implanted proximal to or within the tumor. In one embodiment, the method further comprises repeating steps a, b, c, and/or d until the patient's condition improves. In one embodiment, the anti-cancer agent is a radiotherapeutic agent, such that the radiotherapeutic agent causes ablation of at least one blood vessel feeding said tumor.

Kit of Parts

This invention further relates to a kit of parts comprising an anti-fugetactic agent and at least one anti-cancer agent as described herein. In one embodiment, the kit of parts comprises a first container comprising an anti-fugetactic agent and a second container comprising a chemotherapeutic agent. In one embodiment, the kit of parts comprises a first set of prefilled syringes comprising an injectable form of an anti-fugetactic agent and a second set of prefilled syringes containing an injectable form of a chemotherapeutic agent. In one embodiment, the kit of parts further comprises instructions in a readable medium for dosing and/or administration of the anti-fugetactic agent and at least one anti-cancer agent.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

EXAMPLES

The following examples are for illustrative purposes only and should not be interpreted as limitations of the claimed invention. There are a variety of alternative techniques and procedures available to those of skill in the an which would similarly permit one to successfully perform the intended invention.

Example 1

Mice are injected with tumor cells (subcutaneous injection) from a tumor that expresses high levels of CXCL12 and a tumor allowed to develop. Once the tumor has formed, the mice are injected (subcutaneous in the same flank as the tumor) with AMD3100 or vehicle, once a day for 5 days.

One to three days after the final dose of AMD3100, mice are injected via intraperitoneal injection with 12.5 mg/kg paclitaxel (TAX) or vehicle 18 hours prior to assay of tumor growth. Tumor growth in mice is delayed by TAX treatment, but resumes soon after the treatment is discontinued in mice that were not administered AMD3100. It is contemplated that treatment with AMD3100 prior to treatment with TAX will have a synergistic effect, such that the co-treatment results in a delay in tumor growth that is longer than TAX alone.

What is claimed is:

1. A method for killing a human ovarian cancer cell expressing an amount of a chemokine sufficient to produce a fugetactic effect, which method comprises:
   a) periodically contacting said cell with an effective amount of AMD3100 over a period of about 2 days to about 10 days so as to inhibit said fugetactic effect;
   b) contacting said cell with paclitaxel over a period of about 2 days to about 10 days following the period of administering the AMD3100, wherein steps a) and b) are done in sequential order; and
   c) optionally repeating steps a) and b) as necessary to kill said human ovarian cancer cell.

2. The method of claim 1, wherein said chemokine is CXCL12 or interleukin 8.

3. The method of claim 1, wherein step (b) is initiated within 3 days of completion of contacting the cell with the AMD3100.

4. The method of claim 1, wherein step (b) is initiated the day after completion of contacting the cell with the AMD3100.

5. A method for treating a solid ovarian tumor in a human which tumor expresses a chemokine at a concentration sufficient to produce a fugetactic effect, which method comprises administering to said human an effective amount of AMD3100 over a period of about 2 days to about 10 days so as to inhibit said fugetactic effect, followed by administering to said human paclitaxel over a period of about 2 days to about 10 days following the period of administering the AMD3100.

6. The method of claim 5, wherein said chemokine is CXCL12 or interleukin 8.

7. The method of claim 5, wherein the administering the paclitaxel is initiated within 3 days of administering the AMD3100.

8. The method of claim 5, wherein the administering the paclitaxel is initiated the day after completion of administering the AMD3100.

9. The method of claim 5, wherein metastasis of a cell from the solid ovarian tumor is inhibited.

10. The method of claim 1, wherein the cancer cell is a cancer stem cell in the human, and wherein in step a) the effective amount of the AMD3100 induces the cancer stem cell to enter the circulatory system of the human.

11. The method of claim 5, further comprising the steps of
a) identifying an artery or microartery feeding said solid ovarian tumor;
b) intra-arterially placing a catheter or microcatheter in said artery or microartery proximal to the flow of blood into said solid ovarian tumor wherein said catheter or microcatheter comprising a lumen for delivering a fluid there through and means for delivering said fluid;
c) periodically administering an effective amount of the anti-fugetactic agent through said catheter or said microcatheter to the artery or microartery feeding said solid ovarian tumor so as to inhibit said fugetactic effect; and
d) subsequently administering an effective amount of the anti-cancer agent to the patient.

12. The method of claim 11, wherein step d) further comprises administering the paclitaxel using a catheter, a microcatheter, an external radiation source, or via injection or implantation proximal to or within the solid ovarian tumor.

13. The method of claim 11, further comprising:
e) repeating steps a)-d) until the patient's condition improves.

14. The method of claim 1, further comprising repeating steps a) and b) until the condition of said patient improves.

15. The method of claim 1, wherein the AMD3100 is administered subdermally, intra-arterially, or intravenously.

16. The method of claim 1, wherein the paclitaxel is administered subdermally, intra-arterially, or intravenously.

* * * * *